United States Patent

Nickl et al.

[11] 3,975,524
[45] Aug. 17, 1976

[54] 3-PIPERAZINO-ISOQUINOLINES AND SALTS THEREOF

[75] Inventors: Josef Nickl; Erich Müller; Wolfgang Schröter; Walter Haarmann; Josef Roch, all of Biberach an der Riss, Germany

[73] Assignee: Boehringer Ingelheim GmbH, Ingelheim am Rhein, Germany

[22] Filed: Apr. 11, 1975

[21] Appl. No.: 567,234

[30] Foreign Application Priority Data
Apr. 25, 1974 Germany............... 2420012
Jan. 31, 1975 Germany............... 2503961

[52] U.S. Cl................. 424/246; 424/248; 260/243 B; 260/243 R; 260/247.2 B; 260/247.5 GP
[51] Int. Cl.² ............. A61K 31/54; C07D 279/12
[58] Field of Search...... 260/243 B, 243 R, 247.2 B, 260/247.5 GP; 424/246, 248

[56] References Cited
UNITED STATES PATENTS
3,751,417  8/1973  Allen et al. .................... 260/268

*Primary Examiner*—John M. Ford
*Attorney, Agent, or Firm*—Hammond & Littell

[57] ABSTRACT

Compounds of the formula

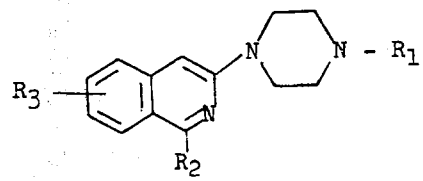

wherein
$R_1$ is hydrogen, alkyl of 1 to 3 carbon atoms, alkanoyl of 1 to 3 carbon atoms, or alkoxycarbonyl of 2 to 4 carbon atoms,
$R_2$ is morpholino, thiomorpholino or 1-oxido-thiomorpholino, and
$R_3$ is hydrogen, fluorine, chlorine, bromine, methyl, methoxy or nitro, and non-toxic, pharmacologicaly acceptable acid addition salts thereof; the compounds as well as the salts are useful as anticoagulants.

8 Claims, No Drawings

3-PIPERAZINO-ISOQUINOLINES AND SALTS THEREOF

This invention relates to novel 3-piperazino-isoquinolines and non-toxic acid addition salts thereof, as well as methods of preparing these compounds.

More particularly, the present invention relates to a novel class of 1-heterocyclic-substituted 3-piperazino-isoquinolines represented by the formula

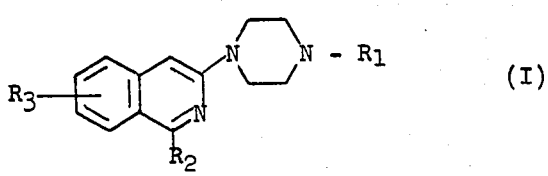

wherein
$R_1$ is hydrogen, alkyl of 1 to 3 carbon atoms, alkanoyl of 1 to 3 carbon atoms, or alkoxycarbonyl of 2 to 4 carbon atoms,
$R_2$ is morpholino, thiomorpholino or 1-oxido-thiomorpholino, and
$R_3$ is hydrogen, fluorine, chlorine, bromine, methyl, methoxy or nitro,
and non-toxic, pharmacologically acceptable acid addition salts thereof.

The compounds embraced by formula I above may be prepared by the following methods:

Method A

By reacting an isoquinoline of the formula

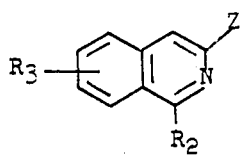

wherein $R_2$ and $R_3$ have the same meanings as in formula I, and Z is a so-called leaving-group, such as halogen, especially chlorine or bromine,
with a piperazine of the formula

wherein $R_1$ has the same meanings as in formula I.

The reaction is performed at temperatures between 100° and 250°C, optionally in the presence of an acid-binding agent, advantageously in the presence of a solvent medium, such as dimethylsulfoxide, phosphoric acid tris-dimethylamide, diphenyl ether, dioxane, glycol dimethyl ether, or a sufficient excess of a piperazine of the formula III, and optionally in a closed vessel.

The reaction may, however, also be carried out in the absence of a solvent. Suitable acid-binding agents include inorganic bases, such as sodium carbonate, potassium carbonate or potassium-tert.butylate, and tertiary organic bases, such as triethylamine or pyridine; the tertiary organic bases may also be used as solvents.

It is advantageous if one imino group in the piperazine reactant of the formula III is protected during the reaction by a conventional protective group, for instance by an acyl group, such as carbethoxy, formyl, acetyl, carbamoyl, benzoyl or toluenesulfonyl. This protective group may, if desired, be subsequently split off, such as by hydrolysis in the presence of an acid or a base, preferably, however, in the presence of a base, such as potassium hydroxide, and at temperatures up to the boiling point of the particular solvent medium which is used.

Method B

For the preparation of a compound of the formula I wherein $R_2$ is 1-oxido-thiomorpholino, by oxidizing a compound of the formula

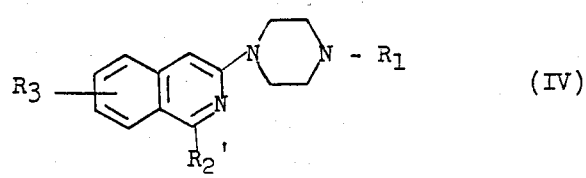

wherein $R_1$ and $R_3$ have the meanings defined above, and $R_2'$ is thiomorpholino.

The oxidation is advantageously carried out with an equimolar amount of an oxidizing agent, such as hydrogen peroxide, peracetic acid, sodium metaperiodate or potassium permanganate, preferably in the presence of a solvent, such as glacial acetic acid, and preferably at temperatures between 0° and 50°C.

In those instances where method A or B yields a compound of the formula I wherein $R_1$ is hydrogen, this compound may, if desired, be converted by alkylation or acylation into the corresponding compound of the formula I wherein $R_1$ has any of the other meaning defined above.

Conversely, if method A or B yields a compound of the formula I wherein $R_1$ is acyl, this compound may, if desired, be converted into the corresponding compound of the formula I wherein $R_1$ is hydrogen by hydrolysis.

Finally, if method A or B yields a compound of the formula I wherein $R_3$ is nitro, this compound may, if desired, be converted by reduction into the corresponding compound of the formula I wherein $R_3$ is amino, which in turn may be converted via a corresponding diazonium salt into the corresponding compound of the formula I wherein $R_3$ has the other meanings defined above.

The compounds embraced by formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, lactic acid, citric acid, tartaric acid, maleic acid, 8-chlorotheophylline or the like.

The preparation of starting compounds of the formulas II and IV is described in Examples A and B below.

The following examples illustrate the present invention and will enable others skilled in the art to understand it more completely. It should be understood, however, that the invention is not limited solely to the particular examples given below.

EXAMPLE A

1-Thiomorpholino-3-chloro-isoquinoline

A mixture of 19.8 gm (0.1 mol) of 1,3-dichloro-isoquinoline [prepared according to S. Gabriel, Berichte 19, 1655 (1886)], 25.8 gm (0.25 mol) of thiomorpholine and 100 ml of dry dioxane was refluxed for 7 hours. Thereafter, the precipitated thiomorpholine hydrochloride was suction-filtered off, the filtrate was evaporated and water was added to the residue. The reaction product was suction-filtered off, dried and recrystallized from ethyl acetate, yielding 18.4 gm (69.5% of theory) of the desired compound, m.p. 133°C. In analogous manner 1-(1-oxido-thiomorpholino)-3-chloro-isoquinoline, m.p. 167°–168°C (from ethyl acetate), was prepared from 1,3-dichloro-isoquinoline and 1-oxido-thiomorpholine.

EXAMPLE B

1-Thiomorpholino-3-chloro-5-methyl-isoquinoline

A mixture of 23.3 gm (0.11 mol) of 1,3-dichloro-5-methyl-isoquinoline [prepared according to G. Simchen et al, Chem. Ber. 102, 3666 (1969); m.p. 120°C], 28.3 gm (0.275 mol) of thiomorpholine and 110 ml of dry dioxane was refluxed for 4 hours. The mixture was then evaporated, the residue was taken up with a mixture of tolune and water, and the toluene phase was isolated, dried and evaporated. The residue was recrystallized from 100 ml of ethyl acetate, yielding 22.7 gm (72% of theory) of the desired compound, m.p. 134°–136°C.

The following starting compounds were prepared in analogous manner:
- a. 1-Morpholino-3-chloro-isoquinoline, m.p. 95°–96°C (from methanol), was prepared from 1,3-dichloro-isoquinoline and morpholine.
- b. 1-Thiomorpholino-3,5-dichloro-isoquinoline, m.p. 141°–143°C (from ethyl acetate), was prepared from 1,3,5-trichloro-isoquinoline and thiomorpholine.
- c. 1-Thiomorpholino-3,7-dichloro-isoquinoline, m.p. 124°–126°C (from n-propanol), was prepared from 1,3,7-trichloro-isoquinoline and thiomorpholine.
- d. 1-Thiomorpholino-3-chloro-5-fluoro-isoquinoline, m.p. 166°–168°C (from ethyl acetate), was prepared from 1,3-dichloro-5-fluoro-isoquinoline and thiomorpholine.
- e. 1-Thiomorpholino-3-chloro-5-methoxy-isoquinoline, m.p. 163°–165°C (from ethyl acetate), was prepared from 1,3-dichloro-5-methoxy-isoquinoline and thiomorpholine.
- f. 1-Thiomorpholino-3-chloro-5-nitro-isoquinoline, m.p. 163°–165°C (from ethyl acetate), was prepared from 1,3-dichloro-5-nitro-isoquinoline [see M. D. Nair and S. R. Mehta, Indian J. Chem. 5, 403 (1967); m.p. 176°–177°C] and thiomorpholine.

EXAMPLE 1

1-Thiomorpholino-3-piperazino-isoquinoline, its maleate and its hydrochloride by method A While stirring, a mixture consisting of 32.8 gm (0.124 mol) of 1-thiomorpholino-3-chloro-isoquinoline, 69 gm (0.8 mol) of anhydrous piperazine and 170 ml of diphenyl ether was heated at 220°C for 16 hours and then at 170°C for 44 hours. After cooling, the mixture was diluted with benzene, and the major amount of unreacted piperazine was removed by washing with water several times. Subsequently, the mixture was extracted with 2 N hydrochloric acid, the acid phase was washed with ethyl acetate, was then made strongly alkaline with sodium hydroxide and was finally extracted with chloroform. After washing, drying and evaporating the chloroform extract, the residue (41.4 gm of free base) was dissolved in 150 ml of methanol and, after addition of 15 gm of maleic acid, precipitated as its crude maleate from 50 ml of methanol. The crude maleate was recrystallized from 1 liter of boiling methanol. Yield: 22.5 gm (42.2% of theory). M.p. 182°–183°C (decomp.).

Analysis: $C_{21}H_{26}N_4O_4S$; mol.wt. 430.53. Calculated: C—58.58%; H—6.08%; N—13.01%; S—7.45%. Found: C—58.90%; H—6.30%; N—12.82%; S—7.32%.

M.p. of the hydrochloride: 245°–247°C (from water).

Analysis: $C_{17}H_{23}ClN_4S$; mol.wt. 350.93. Calculated: C—58.18%; H—6.61%; N—15.96%; Cl—10.11%; S—9.14%. Found: C—58.30%; H—6.63%; N—16.10%; Cl—10.20%; S—9.19%.

M.p. of the free base: 146°–147°C (from methanol/water).

Analysis: $C_{17}H_{22}N_4S$; mol.wt. 314.44. Calculated: C—64.93%; H—7.05%; N—17.82%; S—10.20%. Found: C—65.10%; H—7.06%; N—17.50%; S—10.10%.

EXAMPLE 2

1-(1-Oxido-thiomorpholino)-3-piperazino-isoquinoline and its maleate by method B A solution of 1.1 gm of 30% hydrogen peroxide in 3 ml of acetic acid was added dropwise over a period of 30 minutes to a solution of 3.1 gm (0.01 mol) of 1-thiomorpholino-3-piperazino-isoquinoline in 15 ml of acetic acid, while stirring and cooling on ice. The mixture was then stirred for 2 hours more at room temperature, the solvent was removed in vacuo and the residue was taken up with a mixture of chloroform and sodium hydroxide. After washing and drying of the chloroform phase it was evaporated, and the residue (the free base) was dissolved in methanol. The reaction product was precipitated from the solution as its maleate and recrystallized from methanol. Yield: 2.25 gm (50% of theory). M.p. 194°–196°C (decomp.).

Analysis: $C_{21}H_{26}N_4O_5S$; mol.wt. 446.53. Calculated: C—56.48%; H—5.82%; N—12.54%; S—7.18%. Found: C—56.30%; H—5.97%; N—12.50%; S—7.16%.

M.p. of the free base: 161°–162°C (from isopropanol).

Analysis: $C_{17}H_{22}N_4OS$; mol.wt. 330.46. Calculated: C—61.80%; H—6.71%; N—16.95%; S—9.70%. Found: C—61.70%; H—6.69%; N—17.10%; S—9.54%.

EXAMPLE 3

1-Thiomorpholino-3-piperazino-5-methyl-isoquinoline and its monohydrochloride by method A A mixture of 22.3 gm (0.08 mol) of 1-thiomorpholino-3-chloro-5-methyl-isoquinoline, 34.4 gm (0.4 mol) of anhydrous piperazine and 80 ml of diphenyl ether was heated at 190°C for 28 hours. Subsequently, the diphenyl ether and excess piperazine were almost completely distilled off in vacuo. The residue (the free base) was admixed with water and 8 ml of concentrated hydrochloric acid. The precipitated monohydrochloride was suction filtered off, washed and dried. Yield: 29 gm (99% of theory). M.p. 289°–291°C (from water).

Analysis: $C_{18}H_{22}Cl\ N_4S$; mol.wt. 364.96. Calculated: C—59.26%; H—6.90%; N—15.35%; Cl—9.71%; S—8.78%. Found: C—59.10%; H—7.15%; N—15.40%; Cl—9.80%; S—8.86%.

UV-maxima at
370 nm (log$\epsilon$ = 3.6)
300 nm (log$\epsilon$ = 4.24)
240 nm (log$\epsilon$ = 4.4)

EXAMPLE 4

1-Morpholino-3-piperazino-isoquinoline was prepared analogous to Example 3 from 1-morpholino-3-chloro-isoquinoline and piperazine. M.p. of its hydrochloride: 245°–247°C (from water); yield: 26% of theory.

Analysis: $C_{17}H_{23}Cl\ N_4O$; mol.wt. 334.86. Calculated: C—60.99%; H—6.92%; N—16.73%; Cl—10.59%. Found: C—60.70%; H—7.01%; N—16.80%; Cl—10.70%.

EXAMPLE 5

1-Morpholino-3-(N'-methyl-piperazino)-isoquinoline was prepared analogous to Example 3 from 1-morpholino-3-chloro-isoquinoline by heating with N-methylpiperazine at 200°C. M.p. 130°–131°C (from cyclohexane); yield: 41% of theory.

Analysis: $C_{18}H_{24}N_4O$; mol.wt. 312.42. Calculated: C—69.20%; H—7.74%; N—17.96%. Found: C—69.40%; H—8.00%; N—17.80%.

EXAMPLE 6

1-Thiomorpholino-3-piperazino-5-chloro-isoquinoline was prepared analogous to Example 3 from 1-thiomorpholino-3,5-dichloro-isoquinoline and piperazine by heating in diphenyl ether at 200°C. M.p. of its hydrochloride: 273°–275°C (from water); yield: 97% of theory.

Analysis: $C_{17}H_{22}Cl_2N_4S$; mol.wt. 385.38. Calculated: C—52.97%; H—5.76%; N—14.54%; Cl—18.41%; S—8.32%. Found: C—53.20%; H—5.69%; N—14.26%; Cl—18.25%; S—8.38%.

EXAMPLE 7

1-Thiomorpholino-3-piperazino-7-chloro-isoquinoline was prepared analogous to Example 3 from 1-thiomorpholino-3,7-dichloro-isoquinoline and piperazine by heating in diphenyl ether at 200°C. M.p. of its maleate: 188°–190°C (from ethanol); yield: 85% of theory.

Analysis: $C_{21}H_{25}ClN_4O_4S$; mol.wt. 464.93. Calculated: C—54.26%; H—5.42%; N—12.06%; Cl—7.63%; S—6.86%. Found: C—54.60%; H—5.58%; N—12.32%; Cl—7.81%; S—7.06%.

EXAMPLE 8

1-Thiomorpholino-3-piperazino-5-fluoro-isoquinoline was prepared analogous to Example 3 from 1-thiomorpholino-3-chloro-5-fluoro-isoquinoline by heating for 30 hours with piperazine in diphenyl ether at 200°C. M.p. 213°–215°C (from isopropanol); yield: 90% of theory.

EXAMPLE 9

1-Thiomorpholino-3-piperazino-5-methoxy-isoquinoline was prepared analogous to Example 3 from 1-thiomorpholino-3-chloro-5-methoxy-isoquinoline by heating for 50 hours with piperazine at 190°C in diphenyl ether. M.p. of the hemisulfate: 282°–284°C (decomp., from water). Yield: 41% of theory.

Analysis: $C_{18}H_{24}N_4OS$. ½ $H_2SO_4$; mol.wt. 393.53. Calculated: C—54.94%; H—6.40%; N—14.24%. Found: C—54.80%; H—6.33%; N—14.05%.

EXAMPLE 10

1-Thiomorpholino-3-piperazino-5-nitro-isoquinoline was prepared analogous to Example 3 from 1-thiomorpholino-3-chloro-5-nitro-isoquinoline by heating for 5 hours with piperazine in dioxane at 100°C. M.p. of its hydrochloride: 245°–247°C (from water); yield: 53% of theory.

Analysis: $C_{17}H_{22}ClN_5O_2S$; mol.wt. 395.93. Calculated: C—51.57%; H—5.60%; N—17.69%; Cl—8.90%; S—8.10%. Found: C—51.00%; H—5.60%; N—17.20%; Cl—8.20%; S—8.26%.

EXAMPLE 11

1-Thiomorpholino-3-(N'-acetyl-piperazino)-5-nitro-isoquinoline

First 35.7 gm (0.35 mol) of acetic acid anhydride and then 18.2 gm (0.23 mol) of pyridine were added, while cooling at 20°C, to a solution of 82.5 gm (0.229 mol) of 1-thiomorpholino-3-piperazino-5-nitro-isoquinoline in 750 ml of glycol dimethyl ether. The mixture was stirred for 1 hour at room temperature and then evaporated in vacuo, and the residue was digested with water and recrystallized from n-propanol. M.p. 187°–189°C; yield: 86% of theory.

UV-maxima (in ethanol) at
240 nm (log$\epsilon$ = 4.29)
290 nm (log$\epsilon$ = 4.21)
Infl. 340 nm (log$\epsilon$ = 3.9)

EXAMPLE 12

1-(1-Oxido-thiomorpholino)-3-piperazino-5-methyl-isoquinoline 8.4 gm (0.086 mol) of 34.8% hydrogen peroxide were added dropwise to a suspension of 28.5 gm (0.078 mol) of 1-thiomorpholino-3-piperazino-5-methyl-isoquinoline hydrochloride in 160 ml of 2 N sulfuric acid at 0°C, and the mixture was stirred for 2 hours at 15°–20°C. The mixture was then made alkaline with concentrated sodium hydroxide and exhaustively extracted with a mixture of chloroform and ethanol (3:1). The organic phase was isolated, washed with water and sodium chloride solution, dried and evaporated, and the residue was recrystallized from 150 ml of isopropanol. Yield: 11.6 gm (43% of theory); m.p. 201°–203°C.

Analysis: $C_{18}H_{24}N_4OS$; mol.wt. 344.49. Calculated: C—62.76%; H—7.03%; N—16.25%; S—9.31%.

Found: C—62.60%; H—7.10%; N—16.43%; S—9.30%.

UV-maxima (in ethanol) at
245 nm (logε = 4.41)
305 nm (logε = 4.20)
370 nm (logε = 3.65)

EXAMPLE 13

1-(1-Oxido-thiomorpholino)-3-piperazino-5-chloro-isoquinoline was prepared analogous to Example 12 from 1-thiomorpholino-3-piperazino-5-chloro-isoquinoline in dilute sulfuric acid by oxidation with hydrogen peroxide. M.p. 215°–217°C (from n-propanol); yield: 31% of theory.

Analysis: $C_{17}H_{21}ClN_4OS$; mol.wt. 364.91. Calculated: C—55.96%; H—5.81%; N—15.36%; Cl—9.72%; S—8.78%. Found: C—55.60%; H—5.76%; N—15.30%; Cl—9.87%; S—8.72%.

UV-maxima (in ethanol) at
245 nm (logε = 4.35)
310 nm (logε = 4.21)
380 nm (logε = 3.64)

EXAMPLE 14

1-(1-Oxido-thiomorpholino)-3-piperazino-7-chloro-isoquinoline was prepared analogous to Example 12 from 1-thiomorpholino-3-piperazino-7-chloro-isoquinoline by oxidation with hydrogen peroxide in glacial acetic acid. M.p. 209°–211°C; yield: 13% of theory.

UV-maxima (in ethanol) at
245 nm (logε = 4.35)
310 nm (logε = 4.16)
380 nm (logε = 2.04)

EXAMPLE 15

1-(1-Oxido-thiomorpholino)-3-piperazino-5-fluoro-isoquinoline was prepared analogous to Example 12 from 1-thiomorpholino-3-piperazino-5-fluoro-isoquinoline by oxidation with hydrogen peroxide in dilute sulfuric acid. M.p. 213°–215°C (from n-propanol/petroleum ether). Yield: 31% of theory.

Analysis: $C_{17}H_{21}FN_4OS$; mol.wt. 348.46. Calculated: C—58.60%; H—6.08%; N—16.08%; S—9.20%. Found: C—58.55%; H—6.26%; N—15.85%; S—9.19%.

UV-maxima (in ethanol) at
250 nm (logε = 4.36)
310 nm (logε = 4.16)
380 nm (logε = 3.16)

EXAMPLE 16

1-(1-Oxido--thiomorpholino)-3-piperazino-5-methoxy-isoquinoline was prepared analogous to Example 12 from 1-thiomorpholino-3-piperazino-5-methoxy-isoquinoline hemisulfate by oxidation with hydrogen peroxide in dilute sulfuric acid. M.p. of its hydrochloride trihydrate: 151°–153°C (decomposition; from isopropanol). Yield: 36% of theory.

Analysis: $C_{18}H_{31}ClN_4O_5S$; mol.wt. 451.00. Calculated: C—47.94%; H—6.93%; N—12.42%; Cl—7.86%; S—7.11%. Found: C—47.05%; H—7.03%; N—12.48%; Cl—7.77%; S—7.53%.

UV-maxima (in ethanol) at
242 nm (logε = 4.28)
310 nm (logε = 4.16)
370 nm (logε = 2.93)

EXAMPLE 17

1-(1-Oxido-thiomorpholino)-3-piperazino-5-nitro-isoquinoline was prepared analogous to Example 12 from 1-thiomorpholino-3-piperazino-5-nitro-isoquinoline hydrochloride by oxidation with hydrogen peroxide in dilute sulfuric acid. M.p. of its maleate: 231°–233°C (from isopropanol). Yield: 41% of theory.

Analysis: $C_{21}H_{25}N_5O_7S$; mol.wt. 491.54. Calculated: C—51.32%; H—5.12%; N—14.25%; S—6.52% Found: C—51.30%; H—5.14%; N—14.25%; S—6.49%

UV-maxima (in ethanol) at
240 nm (logε = 4.31)
290 nm (logε = 4.17)
Infl. 340 nm (logε = 3.69)

EXAMPLE 18

1-(1-Oxido-thiomorpholino)-3-N-acetylpiperazino-isoquinoline was prepared analogous to Example 11 from 1-(1-oxido-thiomorpholino)-3-piperazino-isoquinoline and acetic acid anhydride. M.p. 135°–137°C (from benzene); yield: 22% of theory.

EXAMPLE 19

1-Morpholino-3-(N'-formyl-piperazino)-isoquinoline was prepared analogous to Example 5 from 1-morpholino-3chloro-isoquinoline by heating with N-formyl-piperazine. M.p. 121°–122°C (from carbon tetrachloride/cyclohexane). Yield: 32% of theory.

EXAMPLE 20

1-(1-Oxido-thiomorpholino)-3-(N'-acetyl-piperazino)-5-methylisoquinoline was prepared analogous to Example 5 from 1-(1-oxido-thiomorpholino)-3-chloro-5-methyl-isoquinoline by heating with N-acetyl-piperazine. M.p. 201°–202°C (from isopropanol). Yield: 65% of theory.

EXAMPLE 21

1-(1-Oxido-thiomorpholino)-3-(N'-carbethoxy-piperazino)-5-methyl-isoquinoline was prepard analogous to Example 5 from 1-(1-oxido-thiomorpholino)-3-chloro-5-methyl-isoquinoline by heating with N-carbethoxy-piperazine. M.p. 227°–229°C (from n-propanol). Yield: 40% of theory.

EXAMPLE 22

1-(1-Oxido-thiomorpholino)-3-(N'-methyl-piperazino)-5-methylisoquinoline

A mixture of 0.70 gm (2 millimols) of 1-(1-oxidothiomorpholino)-3-piperazino-5-methyl-isoquinoline, 0.18 gm (4 millimols) of formic acid, 0.17 gm of 40% formalin (2.2 millimols) and 10 ml of dioxane was boiler for 2 hours. Subsequently, the mixture was evaporated in vacuo, the residue was made alkaline, and the reaction product was isolated by extraction with ethyl acetate. After evaporation of the extract solution, the residue was recrystallized from 5 ml of benene. M.p. 180°–182°C; yield: 0.20 gm (36% of theory)

EXAMPLE 23

1-(1-Oxido-thiomorpholino)-3-(N'-methyl-piperazino)-5-methylisoquinoline was prepared analogous to Example 5 from 1-(1-oxido-thiomorpholino)-3-chloro-methyl-isoquinoline by heating with N-methyl-piperazine. M.p. 181°–183°C.

EXAMPLE 24

1-(1-Oxido-thiomorpholino)-3-piperazino-5-methyl-isoquinoline 1.0 gm (2.6 millimols) of 1-(1-oxido-thiomorpholino)-3-(N'-acetyl-piperazino)-5-methyl-isoquinoline and 500 mgm of finely pulverized potassium hydroxide were boiled in isopropanol for 3 hours. Thereafter, the mixture was evaporated, and the residue was taken up with a mixture of water and ethyl acetate. The organic phase was isolated, washed, dried and evaporated, and the residue was recrystallized from isopropanol. Yield: 600 mgm (67% of theory); m.p. 200°–202°C.

The compounds of the present invention, that is, those embraced by formula I above and their non-toxic, pharmacologically accepatable acid addition salts, have useful pharmacodynamic properties. More particularly, the compounds of this invention, while producing only a minor effect on the circulation, exhibit a very strong inhibiting effect upon thrombocyte aggregation and platelet stickiness, as well as a prolonging effect upon the bleeding time in warm-blooded animals, such as cats and mice; therefore, they are useful as antithrombotics and anticoagulants.

The above-indicated pharmacodynamic activities were ascertained by the standard pharmacological test methods described below, and the tables show the results obtained from these tests for a representative number of compounds of the present invention, namely:

A = 1-Thiomorpholino-3-piperazino-isoquinoline,
B = 1-(1-Oxido-thiomorpholino)-3-piperazino-isoquinoline,
C = 1-Morpholino-3-(N'-methyl-piperazino)-isoquinoline,
D = 1-(1-Oxido-thiomorpholino)-3-piperazino-5-methyl-isoquinoline,
E = 1-(1-Oxido-thiomorpholino)-3-piperazino-5-chloro-isoquinoline and
F = 1-(1-Oxido-thiomorpholino)-3-piperazino-5-methoxy-isoquinoline.

1. The inhibiting effect upon the platelet stickiness was determined by means of the so-called retention test according to Morris [see E. Deutsch et al, 1. Internationales Symposium uber Stoffwechsel und Membranpermeabilitat von Erythrocyten und Thrombocyten, Vienna, Austria (1969); Georg Thieme Verlag, Stuttgart, Germany]. 1 ml of human citrate-blood is pipetted into each of a number of small test tubes, and the test compound is added to various final concentrations. The tubes are incubated for 10 minutes at 37°C. 1 gm of glass beads (glass beads for gas-chromatography) is added to half of the tubes. Finally, the closed tubes are attached to a vertical wheel and rotated for 1 minute. By this means good contact is obtained between the glass beads and the blood. The tubes are then allowed to stand at room temperature for another hour, after which time a satisfactory sedimentation of erythrocytes has taken place. 0.01 ml of the supernatant plasma is removed, diluted to 1:8,000 with celloscope solution, and the platelet count is read in the celloscope.

TABLE I

| Compound | Concentration Mol/liter | Inhibition in % |
|---|---|---|
| A | $3 \times 10^{-5}$ | 18% |
| B | $3 \times 10^{-5}$ | 33% |
| C | $5 \times 10^{-5}$ | 50% |
| D | $10^{-4}$ | 86% |
| E | $10^{-4}$ | 92% |
| F | $10^{-4}$ | 70% |

2. The inhibiting action upon thrombocyte aggregation was ascertained by the method of Born and Cross, J. Physiol. 170, 397 (1964), in the platelet-rich plasma of healthy human test subjects, by photometrically ascertaining and registering the rate of decrease of the optical density after addition of (a) adenosine diphosphate (ADP). The angle of inclination of the density curve is a measure of the rate of aggregration (V max.). The point on the curve which corresponded to the greatest light-permeability was used for calculation of the optical density (o.D.).

The ADP-doses were held to a minimum, but still sufficiently large to result in an irreversible aggregation. Prior to addition of ADP, each plasma sample was incubated for 10 minutes at 37°C with various amounts of the test compound. From the data thus obtained, the median effective amount of test compound ($ED_{50}$), i.e. the concentration which reduces the maximum light-permeability in platelet-rich plasma after addition of ADP by 50%, was calculated.

TABLE II

| Compound | $ED_{50}$ |
|---|---|
| B | $3 \times 10^{-5}$ mol/l |

(b) Aggregration with collagen

The procedure is the same as described under (a). To provoke aggregation commercial collagen was used, containing 1 mgm of collagen fibrils per 1 ml. To provoke maximum aggregation, about 0.01 ml of this collagen solution was added to 1 ml of platelet-rich plasma. Previously, the plasma was incubated at 37°C with varying quantities of test compound for 10 minutes each:

TABLE III

| Compound | Concentration mol/liter | % inhibition of Vmax | % inhibition of O.D. |
|---|---|---|---|
| A | $10^{-4}$ | 100 | 100 |
|   | $10^{-5}$ | 51 | 62 |
| B | $3.10^{-5}$ | 96 | 96 |
|   | $10^{-5}$ | 75 | 80 |
| D | $3.10^{-5}$ | 100 | 100 |
| E | $10^{-5}$ | 100 | 100 |
| F | $10^{-5}$ | 100 | 100 |

3. The prolonging effect upon the bleeding time was ascertained by the method of Duke, J. Amer. Med. Assoc. 15, 1185 (1910). 10 mgm/kg of the test compound were given per os to non-anesthetized mice. After 1 or 3 hours, about 0.5 mm was cut off from the tail of each animal, and the exuded blood was carefully soaked up with filter paper at intervals of 30 seconds. The number of drops of blood so obtained was used as a measure for the bleeding time compared to untreated animals (5 animals/test).

TABLE IV

| Time after application of compound | % Prolongation of bleeding time for compound | | | | | |
|---|---|---|---|---|---|---|
| | A | B | C | D | E | F |
| 1 hour | 90 | 83 | 85 | 78 | 146 | 117 |
| 3 hours | — | 16 | — | — | — | — |

4. The acute toxicities of the compounds were determined in white mice (observation time: 14 days) after oral or intravenous adminstration. The $LD_{50}$ was calculated from the percentage of animals which died after different doses within the observation time [see Finney et al in *Probit Analysis, third Edition*, Cambridge (1971)].

TABLE V

| Compound | Toxicity | |
|---|---|---|
| B: $LD_{50}$ | 940.0 | mgm/kg p.o. |
| B: $LD_{50}$ | 123.0 | mgm/kg i.v. |
| C: | >250 | mgm/kg p.o.:2 out of 5 animals died |
| D: | >250 | mgm/kg p.o.:0 out of 5 animals died |
| E: | >250 | mgm/kg p.o.:0 out of 5 animals died |

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antithrombotic and anticoagulant dosage unit of the compounds according to the present invention is from 0.083 to 1.67 mgm/kg body weight, preferably 0.16 to 0.84 mgm/kg body weight. The daily dose rate is from 1.66 to 3.34 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 25

Tablets

The tablet composition is compounded from the following ingredients:

| | | |
|---|---|---|
| 1-(1-Oxido-thiomorpholino)-3-piperazino-isoquinoline | | 30.0 parts |
| Lactose | | 38.0 " |
| Potato starch | | 26.0 " |
| Polyvinylpyrrolidone | | 5.0 " |
| Magnesium stearate | | 1.0 " |
| | Total | 100.0 parts |

Preparation:

The isoquinoline compound is intimately admixed with the lactose and the potato starch, the mixture is uniformly moistened with an ethanolic 20% solution of the polyvinylpyrrolidone, the moist mass is forced through a 1.5 mm-mesh screen, and the resulting granulate is dried at 45°C and again passed through a 1.0 mm-mesh screen. The dry granulate thus obtained is admixed with the magnesium stearate, and the composition is compressed into 100 mgm-tablets in a conventional tablet making machine. Each tablet contains 30 mgm of the isoquinoline compound and is an oral dosage unit composition with effective antithrombotic and anticoagulant action.

EXAMPLE 26

Coated Pills

The pill core composition is compounded from the following ingredients:

| | | |
|---|---|---|
| 1-(1-Oxido-thiomorpholino)-3-piperazino-isoquinoline | | 15.0 parts |
| Lactose | | 14.0 " |
| Corn starch | | 8.0 " |
| Polyvinylpyrrolidone | | 2.5 " |
| Magnesium stearate | | 0.5 " |
| | Total | 40.0 parts |

Preparation:

The ingredients are compounded in a manner analogous to that described in the preceding example, and the composition is compressed into 40 mgm-pill cores, which are subsequently coated with a thin shell consisting essentially of a mixture of talcum and sugar and finally polished with beeswax. Each coated pill contains 15 mgm of the isoquinoline compound and is an oral dosage unit composition with effective anti-thrombotic and anticoagulant action.

EXAMPLE 27

Hypodermic Solution

The solution is compounded from the following ingredients:

| | | |
|---|---|---|
| 1-(1-Oxido-thiomorpholino)-3-piperazino-isoquinoline | | 10.0 parts |
| Polyethyleneglycol 600 | | 100.0 " |
| Distilled Water | q.s.ad | 2000.0 " by vol. |

Preparation:

The polyethyleneglycol and the isoquinoline compound are dissolved in a sufficient amount of distilled water which had previously been boiled and cooled in an atmosphere of nitrogen; the dissolution is also carried out in an atmosphere of nitrogen. The resulting solution is diluted to the indicated volume with additional pretreated distilled water, and the resulting solution is filled, again in an atmosphere of nitrogen, into brown 2 cc-ampules which are then sterilized for 20 minutes at 120°C and subsequently sealed. The entire operation must be performed in diffused light. Each ampule contains 10 mgm of the isoquinoline compound, and the contents thereof are an injectable dosage unit composition with effective antithrombotic and anticoagulant action.

EXAMPLE 28

Drop Solution

The solution is compounded from the following ingredients:

| | | |
|---|---|---|
| 1-(1-Oxido-thiomorpholino)-3-piperazino-isoquinoline | | 10.0 parts |
| Cane sugar | | 350.0 " |
| Essence of cocoa | | 50.0 " |
| Sorbic acid | | 1.0 " |
| Ethyl alcohol | | 200.0 parts by vol. |
| Polyethyleneglycol 600 | | 100.0 " |
| Distilled water | q.s.ad | 1000.0 " |

Preparation:

The sorbic acid is dissolved in the ethanol, the solution is diluted with an equal volume of distilled water, and the isoquinoline compound is dissolved in the aqueous mixture (solution 1). The cane sugar is dissolved in the remaining amount of distilled water (solution 2). Solution 2, the polyethyleneglycol and the essence of cocoa are stirred into solution 1, and the composition is filtered. The entire operation must be performed in an atmosphere of nitrogen and in diffused light. 1 ml of the filtrate (about 20 drops) contains 10 mgm of the isoquinoline compound is an oral dosage unit composition with effective antithrombotic and anticoagulant action.

Analogous results are obtained when any one of the other isoquinolines embraced by formula I or a non-toxic acid addition salt thereof is substituted for the particular isoquinoline compound in Examples 25 through 28. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

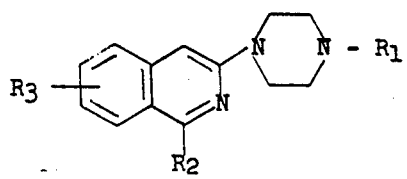

wherein
   $R_1$ is hydrogen, alkyl of 1 to 3 carbon atoms, alkanoyl of 1 to 3 carbon atoms, or alkoxycarbonyl of 2 to 4 carbon atoms,
   $R_2$ is morpholino, thiomorpholino or 1-oxido-thiomorpholino, and
   $R_3$ is hydrogen, fluorine, chlorine, bromine, methyl, methoxy or nitro,
or a non-toxic, pharmacologically acceptable acid addition salt thereof.

2. A compound of claim 1, which is 1-morpholino-3-(N'-methyl-piperazino)-isoquinoline or a non-toxic, pharmacologically acceptable acid addition salt thereof.

3. A compound of claim 1, which is 1-(1-oxido-thiomorpholino)-3-piperazino-5-methyl-isoquinoline or a non-toxic, pharmacologically acceptable acid addition salt thereof.

4. A compound of claim 1, which is 1-(1-oxido-thiomorpholino)-3-piperazino-5-chloro-isoquinoline or a non-toxic, pharmacologically acceptable acid addition salt thereof.

5. A compound of claim 1, which is 1-(1-oxido-thiomorpholino)-3-piperazino-isoquinoline or a non-toxic, pharmacologically acceptable acid addition salt thereof.

6. A compound of claim 1, which is 1-(1-oxido-thiomorpholino)-3-piperazino-5-methoxy-isoquinoline or a non-toxic, pharmacologically acceptable acid addition salt thereof.

7. An anti-thrombotic and anticoagulant pharmaceutical dosage unit composition, consisting essentially of an inert pharmaceutical carrier and an effective antithrombotic and anticoagulant amount of a compound of claim 1.

8. The method of inhibiting thromboses and coagulation of the blood in a warm-blooded animal in need of such treatment, which comprises perorally or parenterally administering to said animal an effective antithrombotic and anticoagulant amount of a compound of claim 1.

* * * * *